United States Patent
Froehlich

(10) Patent No.: US 8,909,313 B2
(45) Date of Patent: Dec. 9, 2014

(54) DEVICE FOR DIAGNOSIS AND/OR THERAPY OF PHYSIOLOGICAL CHARACTERISTICS OF A SELECTED PORTION OF A BODY BY OPTICAL REFLECTANCE OR OPTICAL TRANSMISSION

(75) Inventor: Jürg Froehlich, Zürich (CH)

(73) Assignee: NeMoDevices AG, Kilchberg (CH)

(*) Notice: Subject to any disclaimer, the term of this patent is extended or adjusted under 35 U.S.C. 154(b) by 776 days.

(21) Appl. No.: 13/119,325

(22) PCT Filed: Sep. 4, 2009

(86) PCT No.: PCT/EP2009/006410
§ 371 (c)(1),
(2), (4) Date: Apr. 27, 2011

(87) PCT Pub. No.: WO2010/034398
PCT Pub. Date: Apr. 1, 2010

(65) Prior Publication Data
US 2011/0196241 A1    Aug. 11, 2011

(30) Foreign Application Priority Data

Sep. 25, 2008 (EP) .................................. 08016828

(51) Int. Cl.
*A61B 5/1455* (2006.01)
*A61B 5/00* (2006.01)
A61B 5/145 (2006.01)
A61B 5/1468 (2006.01)

(52) U.S. Cl.
CPC ........... *A61B 5/6833* (2013.01); *A61B 5/14532* (2013.01); *A61B 5/1468* (2013.01); *A61B 5/14552* (2013.01)
USPC ............ 600/344; 600/310; 600/322; 600/323

(58) Field of Classification Search
CPC ........................ A61B 5/14552; A61B 5/14551
USPC ................................................. 600/309–344
See application file for complete search history.

(56) References Cited

U.S. PATENT DOCUMENTS

| 4,223,680 A | 9/1980 | Jobsis |
| 4,321,930 A | 3/1982 | Jobsis et al. |

(Continued)

FOREIGN PATENT DOCUMENTS

| EP | 1 301 119 B1 | 6/2005 |
| WO | WO 92/21281 | 12/1992 |

(Continued)

OTHER PUBLICATIONS

International Preliminary Report on Patentability, mailed Apr. 7, 2011, of corresponding international application No. PCT/EP2009/006410, filed Sep. 4, 2009.

(Continued)

*Primary Examiner* — Eric Winakur
*Assistant Examiner* — Marjan Fardanesh
(74) *Attorney, Agent, or Firm* — Alston & Bird LLP

(57) ABSTRACT

The invention relates to a device for diagnosis and/or therapy of a selected portion of a body by optical reflectance or optical transmission. The device according to the invention has a laminar body (12) containing a tissue-facing surface (13). The laminar body (12) integrally forms a transmitter opening destined to accommodate a transmitter fiber terminal (24) and a receiver opening destined to accommodate a receiver fiber terminal (38a, 38b). Furthermore, it contains annular light shielding means for shielding said transmitter fiber terminal (24) and receiver fiber terminal (38a, 38b) from ambient light sources. Thereby, said annular transmitter and receiver light shielding means are formed as an annular transmitter light shielding bulge (46) and an annular receiver light shielding bulge (48a, 48b), respectively, which are firmly arranged with respect to said laminar body (12), whereby their free ends are protruding with respect to said tissue-facing surface (13) of said laminar body (12).

16 Claims, 5 Drawing Sheets

(56) References Cited

U.S. PATENT DOCUMENTS

| | | | |
|---|---|---|---|
| 4,510,938 A | 4/1985 | Jöbsis et al. | |
| 5,217,013 A | 6/1993 | Lewis et al. | |
| 5,465,714 A * | 11/1995 | Scheuing | 600/323 |
| 5,584,296 A | 12/1996 | Cui et al. | |
| 6,041,247 A * | 3/2000 | Weckstrom et al. | 600/323 |
| 6,343,177 B1 | 1/2002 | Estoque et al. | |
| 6,458,862 B1 | 10/2002 | Musso et al. | |
| 6,606,509 B2 | 8/2003 | Schmitt | |
| 7,047,054 B2 | 5/2006 | Benni | |
| 7,072,701 B2 | 7/2006 | Chen et al. | |
| 7,313,427 B2 | 12/2007 | Benni | |
| 7,613,489 B2 | 11/2009 | Myers | |
| 7,899,510 B2 * | 3/2011 | Hoarau | 600/344 |
| 2006/0058594 A1 * | 3/2006 | Ishizuka et al. | 600/310 |
| 2007/0142717 A1 | 6/2007 | Lowery et al. | |

FOREIGN PATENT DOCUMENTS

| | | |
|---|---|---|
| WO | WO 94/12096 A1 | 6/1994 |
| WO | WO 2008/039392 | 4/2008 |

OTHER PUBLICATIONS

International Search Report, mailed Oct. 16, 2009, of corresponding international application No. PCT/EP2009/006410, filed Sep. 4, 2009.

Written Opinion, mailed Oct. 16, 2009, of corresponding international application No. PCT/EP2009/006410, filed Sep. 4, 2009.

* cited by examiner

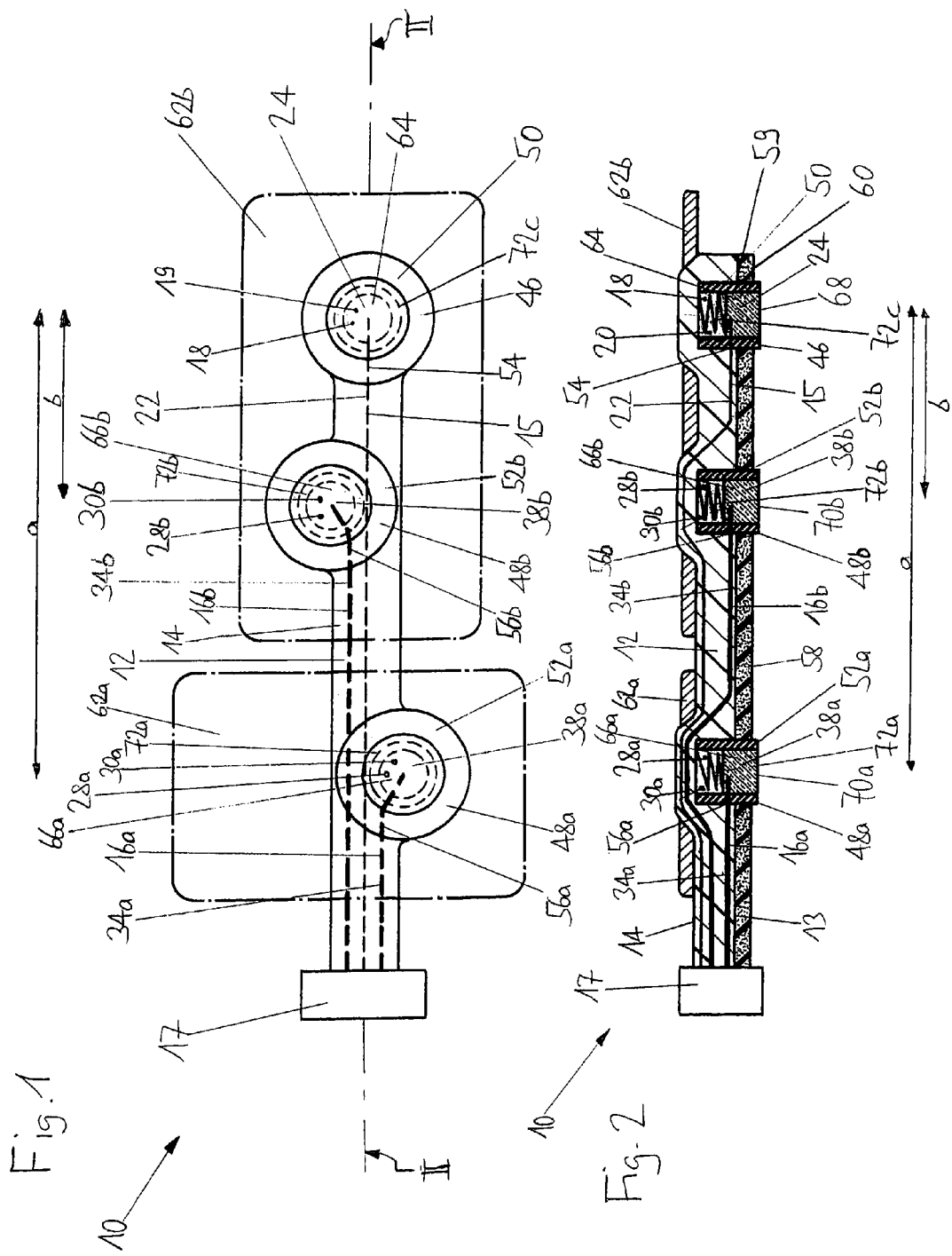

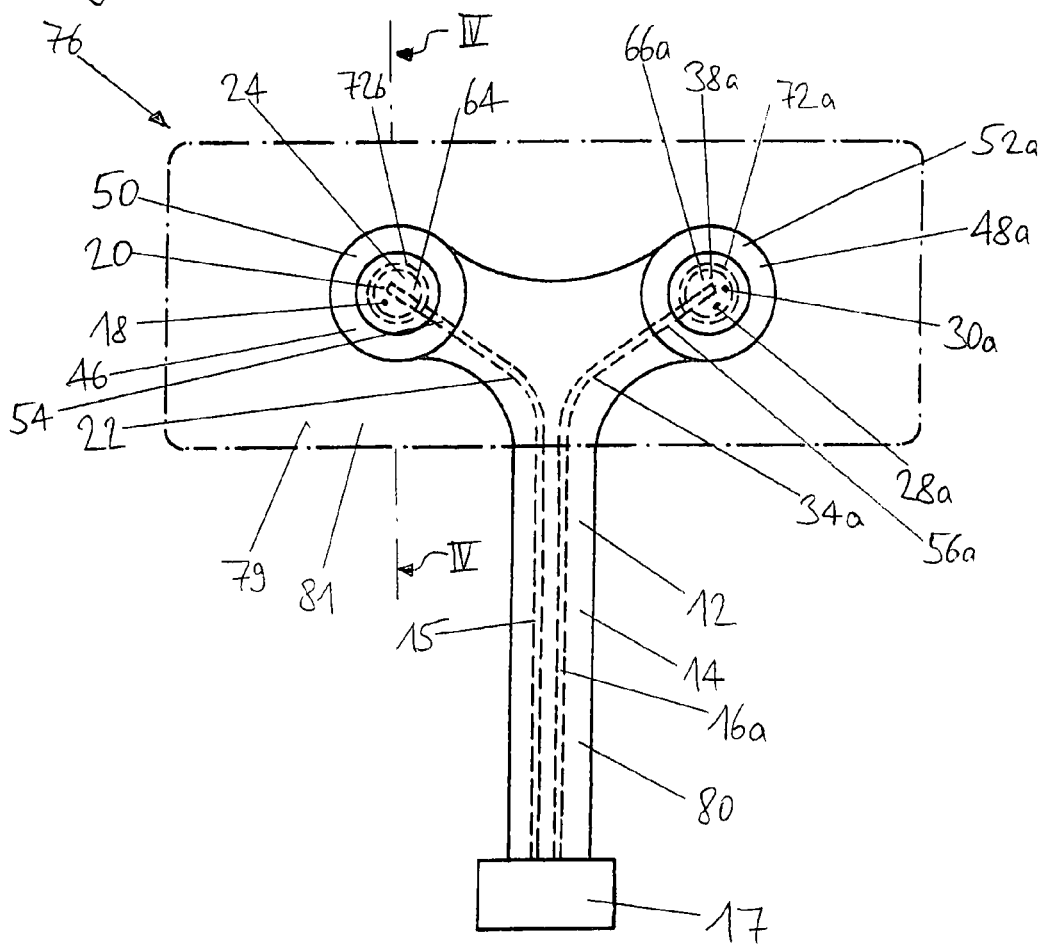
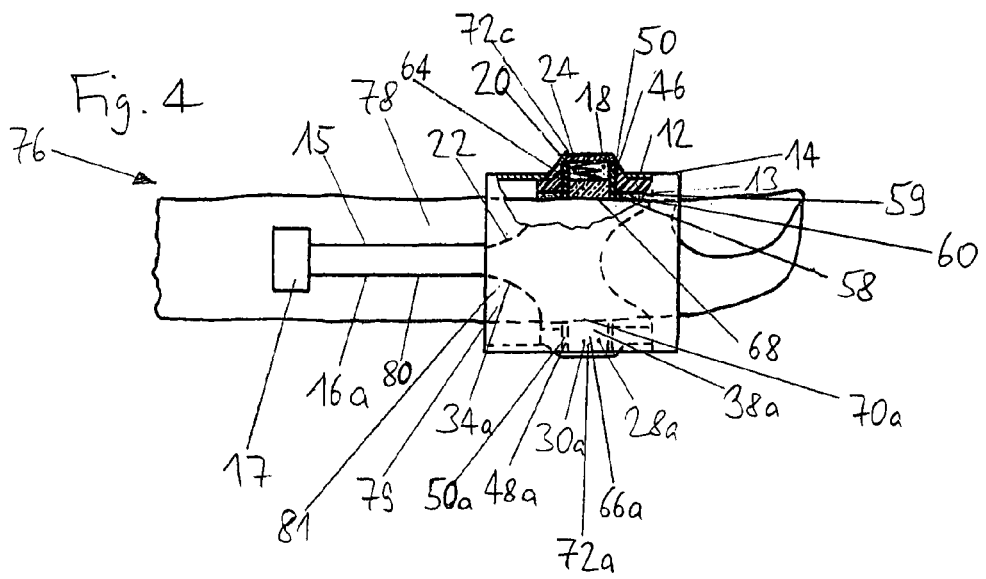

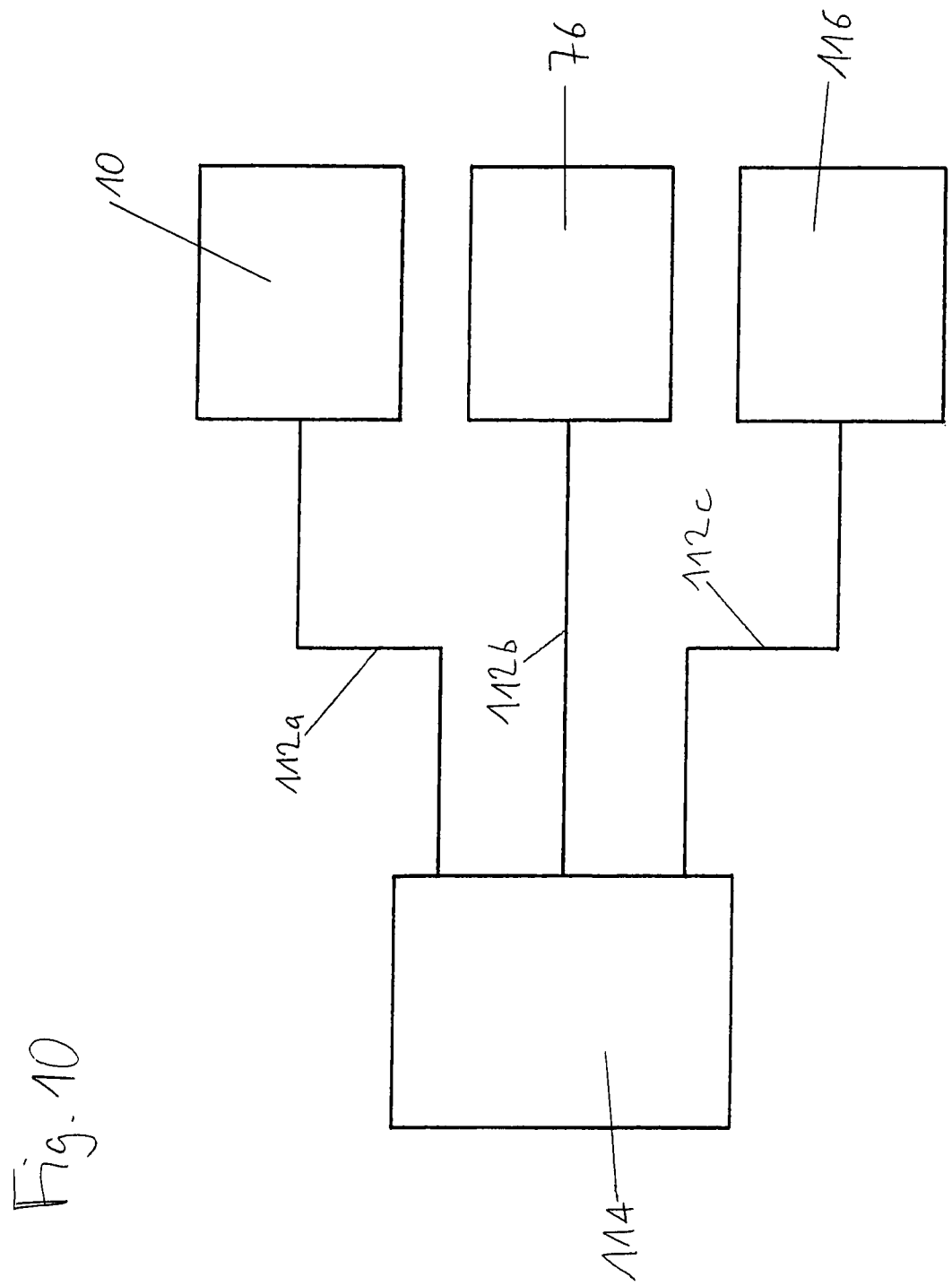

DEVICE FOR DIAGNOSIS AND/OR THERAPY OF PHYSIOLOGICAL CHARACTERISTICS OF A SELECTED PORTION OF A BODY BY OPTICAL REFLECTANCE OR OPTICAL TRANSMISSION

CROSS REFERENCE TO RELATED APPLICATIONS

This application is a national stage application, filed under 35 U.S.C. §371, of International Application No. PCT/EP2009/006410, filed Sep. 4, 2009, which claims priority to European Patent Application No. 08016828.9, filed Sep. 25, 2008, all of which are hereby incorporated by reference in their entirety.

BACKGROUND OF THE INVENTION

1. Field of Invention

The present invention relates to a device for diagnosis and/or therapy of a selected portion of a body by optical reflectance or optical transmission, according to the preamble of claim 1.

Monitoring of certain physiological characteristics of a patient is an inevitable tool in medicine for diagnosis and therapy. Thus, a variety of devices has been developed for measuring such characteristics.

The technique of near infrared spectroscopy (NIRS) is used for various applications, amongst others for monitoring hemodynamics and oxygenation of a selected portion of a body, as e.g. of a specific organ like the brain. Thereby, light in the near infrared spectral domain is emitted into the selected portion of tissue of the body by a light transmitter means. A light receiver means detects the amount of transmitted and/or reflected light. The ratio of absorbed and scattered light with respect to the emitted light can then be determined, from which one or more of the above mentioned physiological characteristics can be calculated.

2. Description of Related Art

Such a device applicable for NIRS measurements is disclosed in U.S. Pat. No. 4,510,938. An assembly of the device includes a base support pad having two socket holes in which module sockets can be installed. These module sockets are formed with an open base end and provide housings for so called optical modules. Each optical module includes an optical fibre cable made up of a bundle of optical fibres which couples through quick disconnect optical coupling, leading directly to a light source and a processing circuitry. Within the optical modules, the optical fibres terminate with a right angle shaped terminal end destined for deflecting an optical light signal at least approximately of an angle of 90°. The terminal end has a slightly protruding portion with respect to the open base end of the module socket, establishing a ground optical face. Furthermore, the terminal end of the fibre bundles can provide both, a near-infrared light source terminal destined for bringing light to the point of light entry of the selected portion of the body, or a near-infrared light detector terminal being destined for collecting and transmitting reflected/transmitted light for further processing and calculations.

The optical modules can be fully nested in their respective module sockets. Therefore, the module sockets include an open slot for receiving the optical fibre cable of the optical module which leads to the light source and the processing circuitry.

Furthermore, the base support pad is formed with two parallel slits leading from the socket holes to an edge of the base support pad. These slits are intended, amongst others, for facilitating the assembling of the base support pad and the module sockets together with their respective optical modules. For securing the module sockets on the base support pad, each of the module sockets is provided at the open base end with three radially extending, thin, and flexible tabs. A double sided adhesive tape is attached on each tab as a means for affixing the respective module socket on the base support pad.

Shielding of ambient light from the optical light modules, and especially from the ground optical face, is crucial for an accurate detection of the amount of transmitted and/or reflected light. Thus, e.g. in U.S. Pat. No. 4,510,938, different light shielding means are disclosed. Double-sided, annular-shaped, and pressure sensitive adhesive tapes of light shielding material are employed on the optical modules and are mounted around the respective ground optical faces in order to provide the desired shielding of ambient light. Additionally, when the optical modules are assembled in their respective module sockets which are affixed by the three radially extending tabs on the base support tab, an auxiliary pad composed of light shielding material which is provided with double-sided adhesive tape is firmly secured over the module sockets and the optical cables. Finally, an overall light shielding cape is affixed over the whole assembly.

A different embodiment compared to the optical modules as described above is disclosed in U.S. Pat. No. 6,343,177 where an integrated fibre terminal and reflector system are presented for transmitting and/or receiving optical signals that are off-axis relative to a terminated optical fibre. Thereby, at least an approximately right angle shaped deflection of the optical signal is accomplished by said optical reflector system without the need for bending the optical fibre within the fibre terminal.

A further embodiment of a device for measuring cerebral hemodynamics and oxygenation invasively is disclosed in EP 1 301 119. It uses passive illuminating and receiving means, i.e. at least two optical transmission means, each comprising one or more optical fibres. A first transmission means transmits light from its proximal to its distal end, i.e. from a light source to a patients head and brain tissue. A second transmission means transmits light from its distal to its proximal end, i.e. from the patient's head and brain tissue to a detection unit. The transmission means are encapsulated by a coating forming an elongated, flat structure which fixes the spatial arrangement of the transmission means. Thereby, the distal end of each transmission means is connected to a deflection means encapsulated by the same coating, being at least in a region of entrance respectively exit of the deflection means optically transmissive to light at wavelengths used. The deflection means are destined for deflecting light transmitted by the transmission means from a direction of transmission, preferably by an angle of 60 to 120°. Preferably the light is deflected by approximately 90° with respect to the direction of transmission. Since optical fibres are small in diameter and deflecting means can be manufactured small in size, the device destined for minimal invasive measurements can be assembled with a width of preferably less than about 20 mm and a thickness of preferably less than about 5 mm.

BRIEF SUMMARY OF THE INVENTION

It is an object of the present invention to provide a device for diagnosis and/or therapy of a selected portion of a body by optical reflectance or optical transmission. Thereby, assembling, mounting, and usability of the device is substantially simplified and the device exhibits improved light shielding properties.

The above mentioned and other objects of the present invention are achieved by a device as specified in claim 1.

Preferred embodiments are specified in the dependant claims and disclosed in the description and the drawing.

The device according to the present invention may be used for any non-invasive and invasive method for diagnosis and/or therapy of a selected portion of a body by optical reflectance or optical transmission, preferably using light in the near infrared region of 700 nm to 1300 nm spectral domain.

The device has a laminar body, exhibiting a tissue-facing surface and an exterior surface averted from said tissue-facing surface. The laminar body integrally forms a transmitter cavity and a receiver cavity. Thereby, the transmitter cavity has a transmitter housing portion and a transmitter passage portion, and the receiver cavity has a receiver housing portion and a receiver passage portion. The transmitter passage portion is discharging into the transmitter housing portion, accordingly, the receiver passage portion is discharging into the receiver housing portion.

The transmitter housing portion of the transmitter cavity is destined to accommodate a transmitter fibre terminal containing an optical transmitter fibre, and the receiver housing portion of the receiver cavity is destined to accommodate a receiver fibre terminal containing an optical receiver fibre. Thereby, the transmitter passage portion allows passing there through the optical transmitter fibre, and the receiver passage portion allows passing there through the optical receiver fibre.

Furthermore, the transmitter fibre terminal is designed for directing light incoming through the transmitter fibre towards a direction at least approximately perpendicular to the tissue-facing surface of the laminar body. Accordingly, the receiver fibre terminal is designed for collecting incoming light from and at least approximately perpendicular to the tissue contacting surface 68 in the optical receiver fibre 16a, 16b.

For light shielding, an annular transmitter light shielding bulge and an annular receiver light shielding bulge are formed and firmly arranged with respect to the laminar body. They are destined for shielding ambient light from the transmitter fibre terminal and the receiver fibre terminal, respectively. In order to accomplish this light shielding function, free ends of the light shielding bulges are protruding with respect to the tissue-facing surface of the laminar body.

Since the laminar body integrally forms the transmitter cavity with the transmitter housing portion and the receiver cavity with the receiver housing portion which accommodate the fibre transmitter terminal and the fibre receiver terminal, respectively, the laminar body can be manufactured small in size, with a width probably less than about 15 mm and a thickness less than about 10 mm.

Additionally, there exist small embodiments for the fibre transmitter and the fibre receiver terminals, as e.g. reflective optical terminals according to claims 7 and 8. These reflective optical terminals further support a fabrication of the whole device which is small in size.

All single parts of the device may be assembled before an actual measurement, allowing to sterilize and to prepackage the whole device, completely assembled, e.g. as a single use kit, without the need of assembling single components by an end user before using the, device. Additionally, an optical connector which can be connected, eventually by an optical cable, with an apparatus including light emitting and evaluation means may further simplify a setup procedure Another advantage for the end user is that the annular transmitter light shielding bulge and the annular light receiver shielding bulge are firmly arranged with respect to the laminar body and may be integrally formed by a transmitter sleeve and a receiver sleeve, respectively, according to claim 6. The end user does not have to take care about light shielding issues e.g. by mounting adhesive light shielding tapes.

Thus, assembling, mounting, and usability of the device is strongly simplified, enabling a fail-safe and fast start of operation which is a crucial issue e.g. in the field of intensive care of patients.

The reflective optical transmitter terminal has a transmitter terminal tissue contacting surface and the reflective optical receiver terminal has a receiver terminal tissue contacting surface, both lying on the site and being at least approximately in parallel to the tissue-facing surface of the laminar body. They are destined for getting in contact with the selected portion of the body. Furthermore, as specified in claims 8 to 10, the reflective optical transmitter terminal and the reflective optical receiver terminal can be flexibly supported within their respective housings. Thereby, a spring force may act on said reflective optical transmitter terminal and on said reflective optical receiver terminal in a direction at least approximately perpendicular to said tissue-facing surface. The spring force may effect that the transmitter terminal tissue contacting surface and the receiver terminal tissue contacting surface are slightly protruding or at least are approximately on a same plane with respect to the free ends of the transmitter and receiver light shielding bulges. Therewith, the transmitter terminal tissue contacting surface and the receiver terminal contacting surface are slightly pressed during application against the selected portion of the body providing optimal light emitting and light detecting conditions.

BRIEF DESCRIPTION OF THE FIGURES

The device according to the invention is explained in more details by embodiments illustrated in the drawing, in which FIG. 1 shows schematically a plan view of a device suitable for example for measurements of hemodynamics of a brain by optical reflectance;

FIG. 2 shows schematically an axial cross section of the device of FIG. 1 along sectional line II-II;

FIG. 3 shows schematically a plane view of a device suitable for example for measurements of hemodynamics of a finger by optical transmission;

FIG. 4 shows schematically a plane view and in one part a schematic cross section along sectional line IV-IV of the device of FIG. 3 mounted on a finger;

FIG. 10 shows schematically a schematic setup of most important components for a NIRS measurement.

DETAILED DESCRIPTION OF VARIOUS EMBODIMENTS OF THE INVENTION

Figure 5:
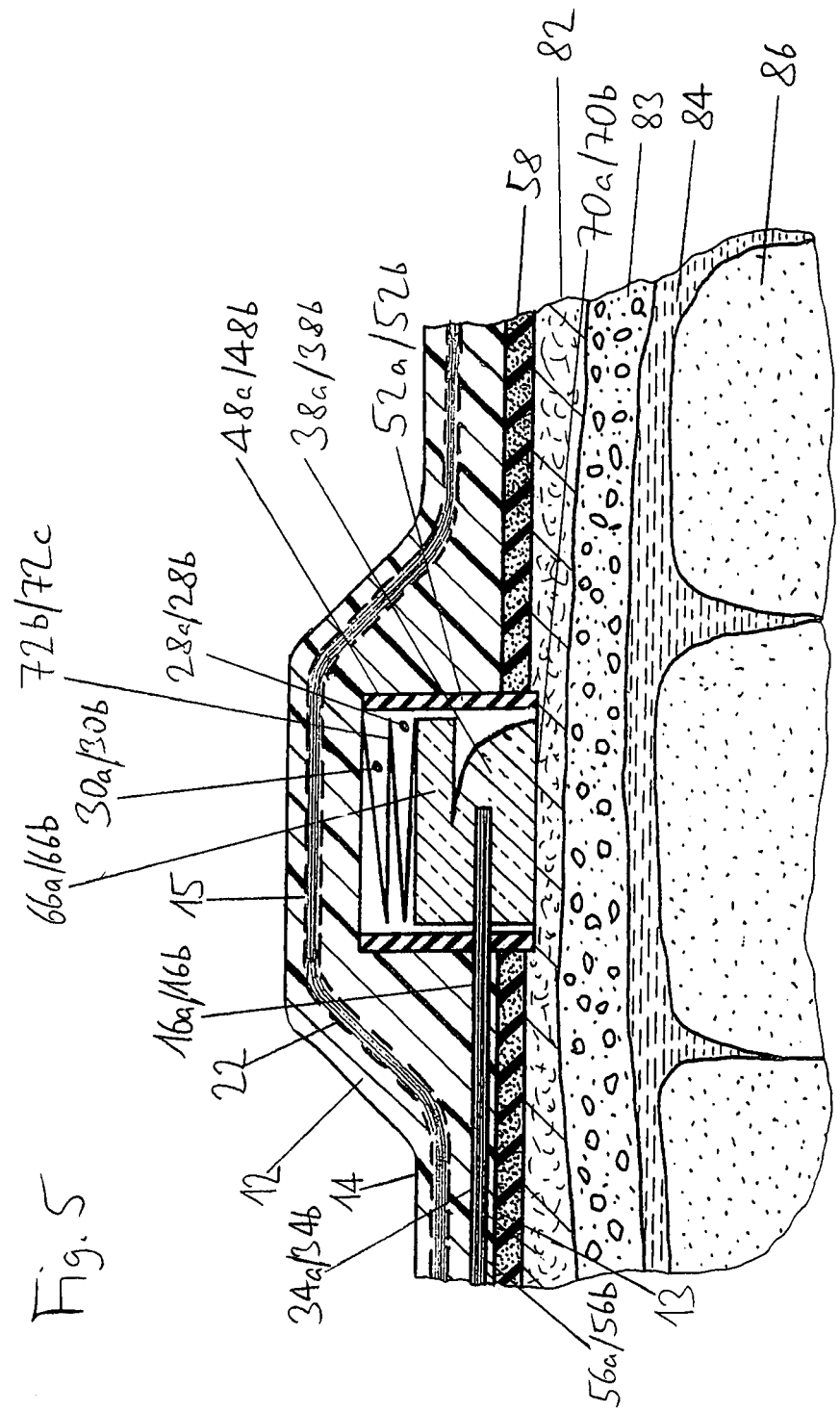
FIG. 5 shows schematically a zoomed part of FIG. 2 whereby a non invasive alignment of a receiver terminal of the device on a scalp is depicted schematically.

FIG. 1 and FIG. 2 show a device 10 adapted for non invasive measurements of hemodynamics and oxygenation of a brain by optical reflectance. The device includes a laminar body 12 in the shape of a band, preferably made of a plastic material, having a tissue-facing surface 13 and an exterior surface 14 averted from the tissue-facing surface 13. The device 10, i.e. an optical transmitter fibre 15 and a first and a second optical receiver fibre 16a, 16b, are connected on one end with an optical connector 17 which is firmly arranged with respect to said laminar body 12. The optical connector 17 interacts as interface between the device 10 and an apparatus for NIRS measurements including light emitting, light detecting, and evaluation means, as e.g. disclosed in EP 1 301 119. Thereby, the optical connector 17 is connected to the apparatus for NIRS measurements either directly or by an optical cable.

The laminar body 12 integrally forms a transmitter cavity 18, located in the free end region of the laminar body 12, opposite to the site on which the optical connector 17 is located. The transmitter cavity. 18 has a transmitter housing portion 20 and a transmitter passage portion 22. Said transmitter passage portion 22 is discharging into said transmitter housing portion 20. The transmitter housing portion 20 is destined to accommodate a transmitter fibre terminal 24 including the optical transmitter fibre 15. The transmitter passage portion 22 allows passing there through the optical transmitter fibre 15, leading through the laminar body 12 from the transmitter housing portion 20 to optical connector 17.

Furthermore, the laminar body 12 integrally forms one or more receiver cavities. In the embodiment depicted in FIG. 1 and FIG. 2, a first receiver cavity 28a and a second receiver cavity 28b are formed. The first receiver cavity 28a is located between the optical connector 17 and the transmitter cavity 18, a distance "a" of at least approximately 4.5 cm away from the transmitter cavity 18. The second receiver cavity 28b is located between the first receiver cavity 28a and the transmitter cavity 18, a distance "b" of at least approximately 1.5 cm away from the transmitter cavity 18. Said distances are adapted for measurements of an adult normal sized brain. For measurements on smaller sized heads, as e.g. heads of newborns, heads with thicker cranial bones or cranial bones with higher bone densities, the distances have to be adapted accordingly.

The first receiver cavity 28a has a first receiver housing portion 30a and a first receiver passage portion 34a, and the second receiver cavity 28b has a second receiver housing portion 30b and a second receiver passage portion 34b. Said first and second receiver passage portions 34a, 34b are discharging into said first and second receiver housing portions 30a, 30b, respectively. The first and second receiver housing portions 30a, 30b are destined to accommodate a first receiver fibre terminal 38a and a second receiver fibre terminal 38b, including the first and the second optical receiver fibres 16a, 16b, respectively. The first and the second receiver passage portions 34a, 34b allow passing there through the first and the second optical receiver fibres 16a, 16b, respectively, leading through the laminar body 12 from the respective first and second receiver housing portion 30a, 30b to the optical connector 17.

The laminar body 12 exhibits—in the top view—button shaped protrusions in regions of the transmitter cavity 18 and the first and second receiver cavities 28a, 28b.

Furthermore, the thickness of the laminar body 12 with respect to the tissue-facing surface 13 is augmented in said regions in order to form said transmitter cavity 18 and said first and second receiver cavities 28a, 28b.

The transmitter housing portion 20 and the first and the second receiver housing portions 30a, 30b are formed as a blind-hole. Furthermore, said transmitter housing portion and said first and second receiver housing portions 30a, 30b are open towards the tissue-facing surface 13 of said laminar body 12.

Preferably, the laminar body 12 is flexible in directions at least approximately perpendicular to the tissue-facing surface 13, allowing a certain adoption of its shape corresponding to a shape of a selected portion of a body, as e.g. to an outer surface of a cranial bone. In directions parallel to the tissue-facing surface 13, the laminar body 12 should exhibit a certain stiffness in order to maintain the spatial arrangement between the transmitter cavity 18 and the first and the second receiver cavities 28a, 28b, i.e. to fix the distance "a" and the distance "b". Furthermore, the laminar body 12 is preferably composed of a material with light shielding properties in order to assist in providing the desired light shielding around the transmitter fibre terminal 24 and the receiver fibre terminals 38a, 38b.

For additional light shielding of the transmitter fibre terminal 24 and the first and the second receiver fibre terminals 38a, 38b, an annular transmitter light shielding bulge 46 and a first and a second annular receiver light shielding bulge 48a, 48b are formed, respectively, firmly arranged with respect to said laminar body 12. Thereby, said annular transmitter light shielding bulge 46 and said first and second annular receiver light shielding bulges 48a, 48b are slightly protruding or are at least approximately on a same plane with respect to said laminar body 12.

A transmitter sleeve 50 and a first and a second receiver sleeve 52a, 52b are arranged within said transmitter housing portion 20 and said first and second receiver housing portions 30a, 30b, respectively. They are firmly affixed with respect to the laminar body 12. Preferably, said transmitter sleeve 50 is extending over at least approximately the entire depth of said transmitter housing portion 20 in a direction at least approximately perpendicular to said tissue-facing surface 13, having a transmitter sleeve through passage portion 54 which allows passing there through the optical transmitter fibre 15. Accordingly, said first and second receiver sleeves 52a, 52b preferably are extending over at least approximately the entire depth of said first and second receiver housing portions 30a, 30b, respectively, in a direction at least approximately perpendicular to said tissue-facing surface 13. The first and second receiver sleeves 52a, 52b have a first and a second receiver sleeve through passage portion 56a, 56b, respectively, which allow passing there through the first and second optical receiver fibres 16a, 16b, respectively. Thereby, the transmitter sleeve 50 and the first and second receiver sleeves 52a, 52b fulfill preferably light shielding functions by shielding the transmitter fibre terminal 24 and the first and second receiver fibre terminals 38a, 38b from ambient light sources.

Said transmitter sleeve 50 and said first and second receiver sleeves 52a, 52b are composed of a resilient, preferably opaque, material, as e.g. black-coloured foam. Furthermore, the annular transmitter light shielding bulge and the first and second annular receiver light shielding bulges 48a, 48b are integrally formed by said transmitter sleeve 50 and said first and second receiver sleeves 52a, 52b, respectively.

Additionally, the laminar body 12 is preferably covered by a foam layer 58, preferably with light absorbing properties, firmly arranged on the tissue-facing surface 13 of the laminar body 12. The foam layer 58 has a laminar body contacting surface 59 facing towards the tissue-facing surface 13 of said laminar body 12 and a foam layer tissue-facing surface 60 averted from said laminar body contacting surface 59. The foam layer 58 is destined for providing additional light shielding. In case of presence of the foam layer, the annular transmitter light shielding bulge 46 and the first and second annular receiver light shielding bulges 48a, 48b are slightly protruding or are at least approximately on a same plane with respect to said foam layer tissue-facing surface 60. Furthermore, an adhesive patch 62a, 62b, laterally protruding with respect to the laminar body 12, is also firmly arranged on the exterior surface 14 of the laminar body 12 in order to affix the device 10 on the selected portion of the body.

In the present embodiment, the transmitter fibre terminal 24 and the first and second receiver fibre terminals 38a, 38b are constructed as a reflective optical transmitter terminal 64 and a first and a second reflective optical receiver terminal 66a, 66b, respectively. The reflective optical transmitter terminal 64 has a transmitter terminal tissue contacting surface 68, preferably planar shaped, and the first and second reflective optical receiver terminals 66a, 66b have a preferably planar shaped first and second receiver terminal tissue contacting surface 70a, 70b, respectively. Preferred embodiments of said reflective optical transmitter and receiver terminals 64, 66a, 66b are depicted and described in more details in FIG. 6-FIG. 9.

The reflective optical transmitter terminal 64 and the first and second reflective optical receiver terminals 66a, 66b can be flexibly supported within the transmitter housing portion 20 of the transmitter cavity 18 and the first and second receiver housing portions 30a, 30b of the first and second receiver cavities 28a, 28b, respectively. A spring force caused by a helical pressure spring 72a, 72b, 72c acting on said reflective optical transmitter terminal 64 and on said first and second reflective optical receiver terminal 66a, 66b in a direction at least approximately perpendicular to the tissue-facing surface of the laminar body 12 effects that the transmitter terminal tissue contacting surface 68 and the first and second receiver terminal tissue contacting surfaces 70a, 70b are slightly protruding or at least are approximately on a same plane with respect to the free ends of the annular transmitter light shielding bulge 46 and of the free ends of the first and the second annular receiver light shielding bulges 48a, 48b. Therewith, during an actual application of the device, the transmitter terminal tissue contacting surface 68 and the first and second receiver terminal tissue contacting surfaces 70a, 70b are slightly pressed against the selected portion of the body, providing optimal light emitting and light detecting conditions, respectively.

For the non invasive measurement of the hemodynamics and oxygenation of a brain using the embodiment of the device 10 as depicted in FIG. 1 and FIG. 2, a first optical signal collected within the first optical receiver fibre 16a originates from light which was emitted into the tissue at the point of the transmitter terminal tissue contacting surface 68 and then was reflected by scalp, cranial bone, cerebrospinal fluid, and brain tissue. A second optical signal collected within the second optical receiver fibre 16b originates from light which was emitted into the tissue at the point of the transmitter terminal tissue contacting surface 68 and then was reflected by at least approximately only the scalp and the cranial bone. From said first and second collected optical signal, a wanted signal originating at least almost only from cerebrospinal fluid and brain tissue can be derived by appropriate calculations.

FIG. 3 and FIG. 4 show a different embodiment of a device 76 suitable for example for measurements of hemodynamics and oxygenation of finger tissue 78 by optical transmission. The device 76 is assembled with the same elements as the device 10 in FIG. 1 and FIG. 2, but, in contrast to the device 10 in FIG. 1 and FIG. 2, the device 76 does not contain the second receiver cavity 28b and all respectively assigned elements. As especially emanating from the schematic cross section part of FIG. 4, the transmitter cavity 18, the transmitter housing portion 20, the transmitter fibre terminal 24 as well as the first receiver cavity 28a, the first receiver housing portion 30a, and the first receiver fibre terminal 38a are equally formed as the respective elements in the device 10. In contrast to the device 10, the laminar body 12 of the device 76 exhibits a T-shaped form, integrally formed by a T-crossbar portion 79 and a T-stringer portion 80, both, the T-crossbar portion 79 and the T-stringer portion 80 having the shape of a band. On a free end region of the T-stringer portion 80, opposite to the T-crossbar portion, the optical connector 17 is firmly affixed with respect to the laminar body 12. The transmitter cavity 18 is arranged on one free end region of the T-crossbar portion 79, whereas the first receiver cavity 28a is arranged on an opposite free end region of the T-crossbar portion 79. Accordingly, the optical transmitter fibre 15, the transmitter passage portion 22 allowing passing there through the optical transmitter fibre 15, the first optical receiver fibre 16a, and the first receiver passage portion 34a allowing passing there through the first optical receiver fibre 16a exhibit also a different line management compared to the embodiment in the device 10 of FIG. 1 and FIG. 2. In the device 76, they are leading through the T-crossbar portion 79 and the T-stringer portion 80 within the laminar body 12, from the transmitter housing portion 20 and the first receiver housing portion 30a, respectively, to the optical connector 17. Instead of a patch for affixing the device on the finger, a velcro strip 81 protruding on each side of the T-crossbar portion 79 of the laminar body 12 can be used. For an accurate measurement of hemodynamics and oxygenation by optical transmission, the distance between the transmitter cavity 18 and the first receiver cavity 28a has to be chosen in such a way that the transmitter cavity 18 is located at least almost directly on the opposite site of the selected portion of the body during the measurement, with respect to the location of the transmitter cavity. Thus, for application of the device 76 on the finger tissue 78, the distance between the transmitter cavity 18 and the first receiver cavity 28a in a flat, unmounted state of the laminar body 12 is at least approximately 1.5 cm, depending on the size of the respective finger.

Figure 9:
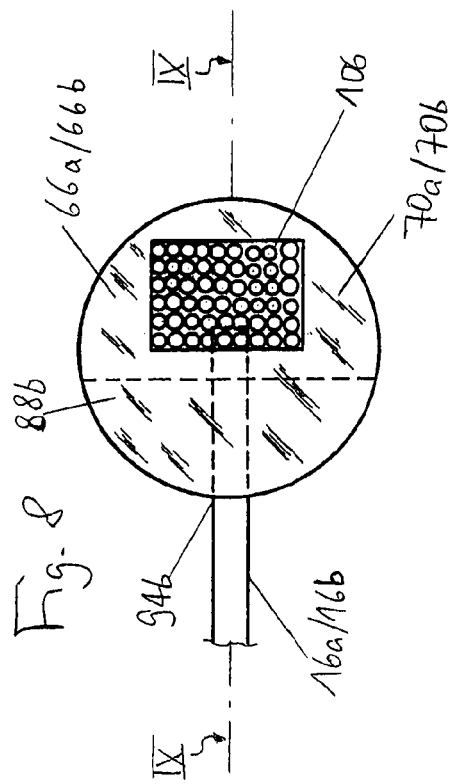
FIG. 9 shows schematically an axial cross section of the reflective optical receiver terminal of FIG. 8 along sectional line IX-IX.

FIG. 5 shows a zoomed part of FIG. 2, namely the first or second reflective optical receiver terminal 38a, 38b including the first or second optical receiver fibre 16a, 16b within the first or second receiver housing portion 30a, 30b of the first or second receiver cavity 28a, 28b. In contrast to an invasive application as shown in FIG. 9 in EP 1 301 119, where a probe is introduced invasively through a burr hole in a skull, FIG. 5 illustrates a possible, non invasive external arrangement of the device 10 on a scalp 82. Thereby, the transmitter cavity 18 as well as the first and the second receiver cavities 28a, 28b with all respective assigned elements are equally mounted and fixated on the scalp as illustrated exemplarily in FIG. 5 with the first or the second receiver cavity 28a, 28b. Thereby, the laminar body is flexibly formed in order to adopt its shape to the shape of the scalp, i.e. the cranial bone, and the distance between the transmitter cavity 18 and the first and second receiver cavities 28a, 28b is fixed. In case of the first optical receiver fibre terminal 38a, light reflected by the scalp 82, cranial bone 83, cerebrospinal fluid 84, and brain tissue 86 of a patient is received, whereas in case of the second optical receiver fibre terminal 38b light reflected at least almost only by the scalp 82 and the cranial bone 83 is received.

Figure 7:
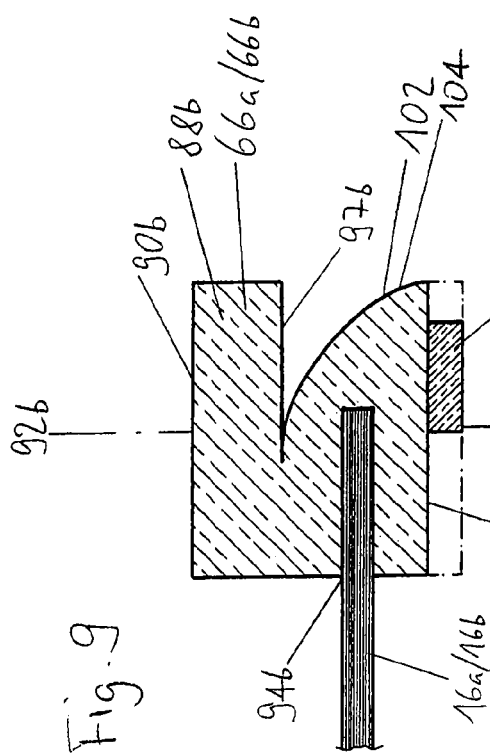
FIG. 7 shows schematically an axial cross section of the reflective optical transmitter terminal of FIG. 6 along sectional line VII-VII.
Figure 6:
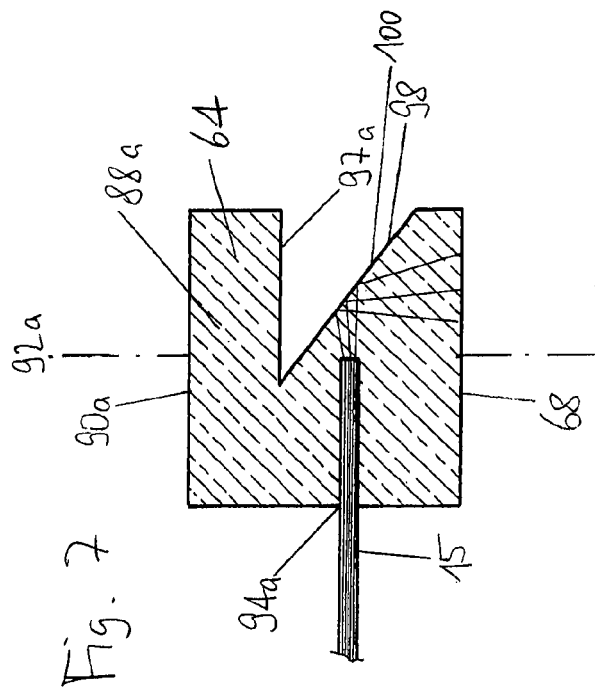
FIG. 6 shows schematically a bottom view of a reflective optical transmitter terminal.

FIG. 6 and FIG. 7 show a preferred embodiment of the reflective optical transmitter terminal 64 in a bottom view and in a cross section, respectively. The reflective optical transmitter terminal 64 is constructed by a circular cylindrical body 88a, preferably composed of a light-transmissive material. It contains on one side the circular transmitter terminal tissue contacting surface 68, which is preferably planar shaped. On the side opposite of and in parallel to said circular transmitter terminal tissue contacting surface 68, the circular cylindrical body contains a preferably planar shaped spring force anchorage surface 90a which provides a contact surface for the helical pressure spring. The main axis 92a of the circular cylindrical body 88a is perpendicular to said circular transmitter terminal tissue contacting surface 68. An end portion of the reflective optical transmitter fibre 15 is enclosed by the circular cylindrical body 88a, whereas the entry point 94a of the optical transmitter fibre 15 into the circular cylindrical body 88a is located at least approximately in the middle of the cylinder barrel. Thereby, the optical transmitter fibre 15 enters in a radial direction, perpendicular to the main axis 92a of the circular cylindrical body 88a, into the circular cylindrical body 88a, running preferably at least almost to the centre of the circular cylindrical body 88a. On the side opposite to said entry point 94a, the circular cylindrical body 88a exhibits a notch 96a defining two planar surfaces, one planar surface 97a in parallel to the transmitter terminal tissue contacting surface 68, the other surface being bevelled 98 with respect to the transmitter terminal tissue contacting surface 68. The bevelled surface 98 is destined for deflecting incoming light from the optical transmitter fibre 15 in a direction at least approximately perpendicular to and towards the transmitter terminal tissue contacting surface 68. Therefore, it exhibits optical light deflection means, preferably a mirror 100.

Figure 8:
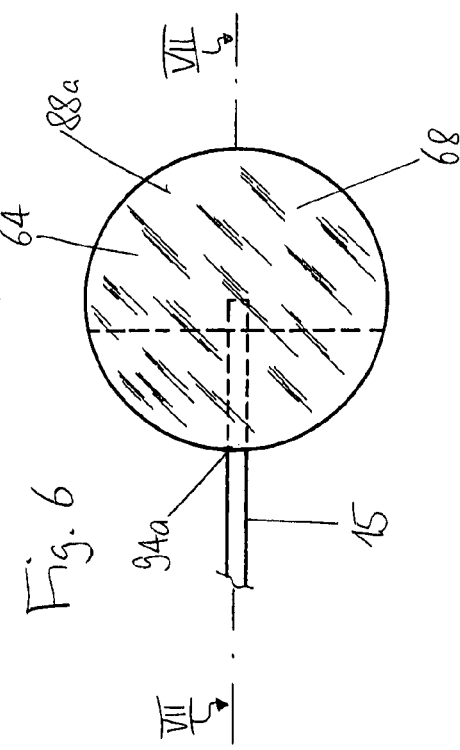
FIG. 8 shows schematically a bottom view of a reflective optical receiver terminal.

FIG. 8 and FIG. 9 show an embodiment of the first and second reflective optical receiver terminals 66a, 66b in a bottom view and in a cross section, respectively. The reflective optical receiver terminal 66a, 66b is constructed by a further circular cylindrical body 88b, preferably composed of a light-transmissive material. It contains on one side the spherical receiver terminal tissue contacting surface 70a, 70b, which is preferably planar shaped. On the side opposite of and in parallel to said circular receiver terminal tissue contacting surface 70a, 70b, the circular cylindrical body 88b contains a further preferably planar shaped spring force anchorage surface 90b which provides a contact surface for the helical pressure spring. The main axis 92b of the circular cylindrical body is perpendicular to said circular receiver terminal tissue contacting surface 70a, 70b. An end portion of the reflective optical receiver fibre 16a, 16b is enclosed by the circular cylindrical body 88b, whereas the entry point 94b of the optical receiver fibre 16a, 16b into the circular cylindrical body 88b is located at least approximately in the middle of the cylinder barrel. Thereby, the optical receiver fibre 16a, 16b enters in a radial direction, perpendicular to the main axis 92b of the circular cylindrical body 88b, into the circular cylindrical body 88b, running preferably at least almost to the centre of the circular cylindrical body 88b. On the side opposite to said entry point 94b, the circular cylindrical body 88b exhibits a further notch 96b defining two further surfaces, one further surface 97b which is planar shaped and in parallel to the receiver terminal tissue contacting surface 70a, 70b, the other exhibiting a concave shaped surface 102. The concave shaped surface 102, preferably acting as a parabolic light reflector, is destined for collecting incoming light from and at least approximately perpendicular to the receiver terminal tissue contacting surface 70a, 70b in the optical receiver fibre 16a, 16b. Thereby, the end portion of the optical receiver fibre is situated at least almost in the focal point of the parabolic light reflector. Therefore, The concave shaped surface optical light deflection means, preferably a concave mirror 104. Additionally, the reflective optical receiver terminal 66a, 66b can be equipped with a grid for eliminating scattered radiation 106 on the receiver terminal tissue contacting surface 70a, 70b.

FIG. 10 schematically shows a possible setup of most important components for a NIRS measurement. Thereby, the device 10 for cerebral measurements, as shown in FIG. 1 and FIG. 2, is connected by a first optical connection cable 112a with an apparatus 114 for NIRS measurements. Thereby, the first optical connection cable 112a contains at least three optical fibres, one for transmitting light from the apparatus 114 to the optical connector 17 of the device 10, i.e. to the optical transmitter fibre 15, and two for transmitting light from the optical connector 17, i.e. from the first and the second optical receiver fibres 16a, 16b of the device 10, to the apparatus 114.

Furthermore, the device 76 for measurements of hemodynamics of the finger tissue, as shown in FIG. 3 and FIG. 4, is also connected with said apparatus 114 by a second optical connection cable 112b. Said second optical connection cable 112b contains at least two optical fibres, one for transmitting light from the apparatus 114 to the optical connector 17 of device 76, i.e. to the transmitter fibre 15, and one for transmitting light from the optical connector 17 of device 76, i.e. from the first optical receiver fibre 16a, to the apparatus 114. Additionally, any or more other devices 116, destined for measuring any additional physiological characteristics, is connected with the apparatus 114, preferably by a third optical cable 112c. Said apparatus 114 for NIRS measurements includes light emitting, light detecting, and evaluation means. It is destined for processing optical signals received from the different connected devices by standard and commonly known evaluation processes.

The device 10 as depicted e.g. in FIGS. 1 and 2 is appropriate for measuring hemodynamics and oxygenation of brain tissue. With modifications, as shown in FIGS. 3 and 4, measurements of hemodynamics and oxygenation of other tissues can be performed, as e.g. shown exemplarily with finger tissue 78. Other modifications of the device 10 or 76, e.g. by omitting the foam layer 58 and the adhesive patch 62a, 62b may allow to measure e.g. invasively hemodynamics and oxygenation of inner organs, like e.g. brain, liver, heart, kidney, bowel, bones, muscles, penis etc. In an invasive application, a measurement with only a first receiver fibre terminal 38a would be sufficiently since a direct application on an organ of interest can be performed. Normally, there is no need to determine and to compensate an interference signal, as e.g. in the exterior application of the device 10 on the scalp 82, where such an interference signal originating from the scalp 82 and the bone layer 83 has to be compensated, as described above. Nevertheless, a measurement with more than one receiver fibre terminal is also feasible in the invasive case, therewith, signals from different depths of the organ of interest can be determined.

Furthermore, instead of measuring hemodynamics and oxygenation of a specific tissue with the device 10 or an accordingly modified device, it is also possible to use said device for measurements of other physiological parameters of said tissue, as e.g. glucose, excitatoric transmitters (e.g. in the brain), inflammatory mediators (e.g. in transplanted organs), different ions (e.g. calcium in the heart) or artificial optical active markers introduced in the body (e.g. associated with tumour labelling) etc.

Furthermore, in another embodiment of device 10, the position of the transmitter cavity 18 and of the first and second receiver cavities 28a, 28b may be permuted, according to the measurement application.

In a preferred embodiment, the transmitter sleeve through passage portion 54 is formed as a transmitter sleeve slot with its main extension in direction at least approximately perpendicular to the tissue-facing surface 13 destined for allowing a greater manoeuvrability of the optical transmitter fibre 15. Accordingly, the receiver sleeve through passage portions 56a, 56b are formed as a receiver sleeve slots with their main extension in direction at least approximately perpendicular to the tissue-facing surface 13 destined for allowing a greater manoeuvrability of the first and the second optical receiver fibres 16a, 16b. The transmitter sleeve slot and the receiver sleeve slots help avoiding a possible damage of the optical transmitter fibre 15 and the first and the second optical receiver fibres 16a, 16b, respectively, caused by the movements of the reflective optical transmitter terminal 64 and the first and the second reflective optical receiver terminals 66a, 66b, due to their flexible support.

Furthermore, a deflection restriction mechanism may be provided destined for restricting the maximum deflection of the reflective optical transmitter terminal 64 within the transmitter housing portion 20 and the maximum deflection of the first and second reflective optical receiver terminals 66a, 66b within the first and second receiver housing portion 30a, 30b. A possible construction of the deflection restriction mechanism is by forming two notches at least approximately perpendicular with respect to the tissue-facing surface 13 of said laminar body 12 on opposite sides of each circular cylindrical body 88a, 88b of said reflective optical transmitter terminal 64 and of said first and second reflective optical receiver terminal 66a, 66b, respectively. A corresponding counterpart, firmly arranged with respect to the laminar body 12, e.g. in form of protruding bulges, engaging in the corresponding notches, thereby effects that the reflective optical transmitter terminal 64 and the first and the second reflective optical receiver terminals 66a, 66b can not be deflected over a predefined, maximum deflection. Instead of the notches formed on each circular cylindrical body 88a, 88b, the planar surface 97a, 97b could also be used as deflection restriction mechanism together with a corresponding counterpart firmly arranged with respect to the laminar body 12, as described above.

Instead of a helical pressure spring 72 causing the spring force acting on said reflective optical transmitter terminal 64 and on said first and second reflective optical receiver terminals 66a, 66b, other spring force like structures can be used, as e.g. a tongue-like spring integrally formed by the laminar body 12.

In another possible embodiment, the transmitter cavity 18 and the first and second receiver cavities 28a, 28b are lined on all sides by the transmitter sleeve 50 and the first and second receiver sleeves 52a, 52b, respectively, except on the side of the tissue-facing surface 13 in order to further enhance light shielding properties around the transmitter fibre terminal 24 and the first and second receiver fibre terminals 38a, 38b. Furthermore, the transmitter housing portion 20 and the first and the second receiver housing portions 30a, 30b, may be covered on the tissue-facing surface 13 of said laminar body 12 by a transparent membrane or a transparent protection film.

In another embodiment, the transmitter light shielding bulge 46 and the first and second receiver light shielding bulges 48a, 48b may be injection moulded on the laminar body 12 and be affixed directly on said laminar body 12.

The invention claimed is:

1. A device for diagnosis and/or therapy of a selected portion of a body by optical reflectance or optical transmission having a laminar body including a tissue-facing surface, an exterior surface averted from said tissue-facing surface, a transmitter opening destined to accommodate a transmitter fibre terminal containing an optical transmitter fibre, and a receiver opening destined to accommodate a receiver fibre terminal containing an optical receiver fibre;

said transmitter fibre terminal being designed for directing light incoming through said optical transmitter fibre towards a direction at least approximately perpendicular to the tissue-facing surface;

said receiver fibre terminal being designed for collecting incoming light from a direction at least approximately perpendicular to said tissue-facing surface in said optical receiver fibre;

annular transmitter light shielding element for shielding said transmitter fibre terminal from ambient light sources;

annular receiver light shielding element for shielding said receiver fibre terminal from ambient light sources;

wherein said transmitter opening is a transmitter cavity having a transmitter housing portion and a transmitter passage portion, said transmitter passage portion discharging into said transmitter housing portion and allowing passing there through said optical transmitter fibre;

said transmitter cavity being integrally formed with said laminar body;

said receiver opening is a receiver cavity having a receiver housing portion and a receiver passage portion, said receiver passage portion discharging into said receiver housing portion and allowing passing there through said optical receiver fibre;

said receiver cavity being integrally formed with said laminar body;

said annular transmitter light shielding element is formed as an annular transmitter light shielding bulge and said annular receiver light shielding element is formed as an annular receiver light shielding bulge; and said annular transmitter light shielding bulge and said annular receiver light shielding bulge are firmly arranged with respect to said laminar body, and their free ends are protruding with respect to said tissue-facing surface of said laminar body.

2. A device according to claim 1, wherein a transmitter sleeve is arranged within said transmitter housing portion, firmly arranged with respect to said laminar body destined for shielding said transmitter fibre terminal from ambient light sources, and a receiver sleeve is arranged within said receiver housing portion, firmly arranged with respect to said laminar body destined for shielding said receiver fibre terminal from ambient light sources.

3. A device according to claim 2, wherein said transmitter sleeve is extending over at least approximately the entire depth of said transmitter housing portion in a direction at least approximately perpendicular to said tissue-facing surface, having a transmitter sleeve through passage portion allowing passing there through said optical transmitter fibre.

4. A device according to claim 2, wherein said receiver sleeve is extending over at least approximately the entire depth of said receiver housing portion in a direction at least approximately perpendicular to said tissue-facing surface, having a receiver sleeve through passage portion, respectively) allowing passing there through said optical receiver fibre.

5. A device according to claim 2, wherein said transmitter sleeve and said receiver sleeve are composed of a resilient material.

6. A device according claim 2, wherein said annular transmitter light shielding bulge is integrally formed by said transmitter sleeve(50) and said annular receiver light shielding bulge is integrally formed by said receiver sleeve.

7. A device according to claim 1, wherein said transmitter fibre terminal has a reflective optical transmitter terminal being arranged in said transmitter housing portion and being in contact with said optical transmitter fibre, and said receiver fibre terminal has a reflective optical receiver terminal being arranged in said receiver housing portion and being in contact with said optical receiver fibre.

8. A device according to claim 7, wherein said reflective optical transmitter terminal is flexibly supported within said transmitter housing portion with respect to deflections at least approximately perpendicular to said tissue-facing surface and said reflective optical receiver terminal is flexibly supported within said receiver housing portion with respect to deflections at least approximately perpendicular to said tissue-facing surface.

9. A device according to claim 8, wherein a spring force in direction at least approximately perpendicular to said tissue-facing surface is acting on said reflective optical transmitter fibre terminal and on said reflective optical receiver fibre terminal, effecting that said reflective optical transmitter fibre terminal is slightly protruding with respect to the free end of said annular transmitter light shielding bulge and said reflective optical receiver fibre terminal is slightly protruding with respect to the free end of said annular receiver light shielding bulge.

10. A device according to claim 9, wherein said spring force is caused by a helical pressure spring firmly arranged with said laminar body or by a tongue-like spring integrally formed with said laminar body.

11. A device according to claim 9, wherein said reflective optical transmitter fibre terminal is at least approximately on a same plane with respect to the free end of said annular transmitter light shielding bulge and said reflective optical receiver fibre terminal is at least approximately on the same plane with respect to the free end of said annular receiver light shielding bulge.

12. A device according to claim 1, wherein said laminar body is covered by a foam layer firmly arranged on said tissue-facing surface.

13. A device according to claim 12, wherein the free end of said annular transmitter light shielding bulge and the free end of said annular receiver light shielding bulge are protruding with respect to the laid-open surface of said foam layer.

14. A device according to claim 12, wherein said foam layer possesses light absorbing properties.

15. A device according to claim 13, wherein the free end of said annular transmitter light shielding bulge and the free end of said annular receiver light shielding bulge are at least approximately on the same plane with respect to the laid-open surface of said foam layer.

16. A device according to claim 1, wherein an adhesive patch is firmly arranged on said exterior surface of said laminar body.

* * * * *